US010966908B2

(12) United States Patent
Allievi

(10) Patent No.: US 10,966,908 B2
(45) Date of Patent: Apr. 6, 2021

(54) DISPENSER OF SUBSTANCE DOSES WITH DISH FOR COLLECTION THEREOF

(71) Applicant: AGEvoluzione S.r.l.s., Pavia (IT)

(72) Inventor: Umberto Allievi, Pavia (IT)

( * ) Notice: Subject to any disclaimer, the term of this patent is extended or adjusted under 35 U.S.C. 154(b) by 0 days.

(21) Appl. No.: 16/138,744

(22) Filed: Sep. 21, 2018

(65) Prior Publication Data

US 2020/0093702 A1    Mar. 26, 2020

(51) Int. Cl.
*A61J 7/00* (2006.01)
*A61J 7/04* (2006.01)
*B65D 83/04* (2006.01)

(52) U.S. Cl.
CPC ........... *A61J 7/0076* (2013.01); *A61J 7/0069* (2013.01); *A61J 7/0418* (2015.05); *B65D 83/0454* (2013.01); *A61J 2200/30* (2013.01)

(58) Field of Classification Search
CPC .... B65D 83/04; B65D 83/0454; A61J 7/0076; A61J 7/0418; A61J 7/0069; A61J 2200/30; A61J 7/0472; A61J 1/035; G01F 11/10; B67D 5/10; B65B 59/00
USPC ............................................. 221/2, 133, 92
See application file for complete search history.

(56) References Cited

U.S. PATENT DOCUMENTS

| | | | | |
|---|---|---|---|---|
| 2,587,928 A | * | 3/1952 | Tuck | B65D 83/0472 221/25 |
| 2,758,710 A | * | 8/1956 | Egmont | B65D 83/0847 221/25 |
| 2,931,536 A | * | 4/1960 | Thomasma | A47K 17/003 221/41 |
| 2,984,397 A | * | 5/1961 | Gillam | B65D 83/0472 225/49 |
| 4,162,739 A | * | 7/1979 | Nelson | B65C 11/00 221/70 |

(Continued)

FOREIGN PATENT DOCUMENTS

| | | |
|---|---|---|
| JP | 2016033033 A | 3/2016 |
| WO | 199005684 A1 | 5/1990 |

(Continued)

*Primary Examiner* — Rakesh Kumar
(74) *Attorney, Agent, or Firm* — John M. Janeway; Janeway Patent Law, PLLC

(57) ABSTRACT

A solution is proposed for dispensing substances to be taken by a user. A corresponding dispensing device comprises a memory for storing an indication of a taking plan of a plurality of doses of one or more substances, the taking plan comprising an indication of a taking time of each dose, a plurality of compartments each one for containing one of the doses, a signaling unit for providing a taking notice of each dose in response to the corresponding taking time, a pushbutton for releasing the dose corresponding to each taking notice from the corresponding compartment in response to a releasing command; the dispensing device comprises a plate having a collecting surface in a central zone thereof, the compartments being arranged in a peripheral zone of the plate and the pushbutton facing towards the central zone of the plate for collecting the doses released thereby onto the collecting surface. An assistance system is also proposed for facilitating the taking of substances by a user, the system comprising this dispensing device and a processing device of a person in charge of the dispenser device adapted to communicate with each other.

6 Claims, 14 Drawing Sheets

(56) References Cited

U.S. PATENT DOCUMENTS

| | | | | |
|---|---|---|---|---|
| 4,361,408 A * | 11/1982 | Wirtschafter | ......... | A61J 7/0472 221/2 |
| 4,712,460 A * | 12/1987 | Allen | .................... | A61J 7/0076 424/443 |
| 4,733,797 A * | 3/1988 | Haber | ................ | B65D 83/0472 221/131 |
| 5,246,299 A * | 9/1993 | Kitsuki | .................... | B41J 17/32 242/343.2 |
| 5,630,347 A * | 5/1997 | Elvio | ........................ | G07F 11/68 74/665 GE |
| 6,085,936 A * | 7/2000 | Friar | .................. | B65D 83/0472 221/25 |
| 6,533,204 B2 * | 3/2003 | Ishihara | ............... | G11B 23/045 242/348.2 |
| 7,424,888 B2 * | 9/2008 | Harvey | ............ | A61M 15/0083 128/203.15 |
| 7,896,192 B2 * | 3/2011 | Conley | ............... | G07F 17/0092 221/15 |
| 7,946,421 B2 * | 5/2011 | Kowalik | ................ | B65D 5/725 206/534 |
| 8,135,497 B2 * | 3/2012 | Joslyn | .................... | A61J 7/0076 700/237 |
| 8,196,774 B1 * | 6/2012 | Clarke | .................... | G07F 11/68 221/197 |
| 8,662,347 B2 * | 3/2014 | Coggins | ................. | A61B 50/22 221/71 |
| 8,939,281 B2 * | 1/2015 | Matsuba | ................ | B65D 25/00 206/1.5 |
| 9,597,261 B2 * | 3/2017 | Baarman | .................. | A61J 7/04 |
| 9,719,628 B2 * | 8/2017 | Sternberg | ............... | B65C 9/1869 |
| 10,279,985 B2 * | 5/2019 | Mills | .................... | A61J 7/0481 |
| 10,292,906 B1 * | 5/2019 | Gershoni | ................ | A61J 7/0427 |
| 2001/0021074 A1 * | 9/2001 | Marquiss | ................ | B01L 9/523 359/892 |
| 2005/0049747 A1 * | 3/2005 | Willoughby | ............... | A61J 7/04 700/232 |
| 2006/0124658 A1 * | 6/2006 | Coe | .......................... | A61J 7/04 221/121 |
| 2007/0261985 A1 * | 11/2007 | Allen | ........................ | A61J 7/04 206/538 |
| 2008/0000799 A1 * | 1/2008 | Arvidsson | ................ | A61J 7/04 206/534 |
| 2008/0179387 A1 * | 7/2008 | Cantlay | ................. | A61J 7/0481 235/375 |
| 2008/0203107 A1 * | 8/2008 | Conley | .................... | G07F 11/16 221/1 |
| 2010/0147867 A1 * | 6/2010 | Villegas Estrada | .... | B65D 50/04 221/87 |
| 2010/0305750 A1 * | 12/2010 | Conley | ................. | A61J 7/0427 700/237 |
| 2011/0226798 A1 * | 9/2011 | Sternbach | .......... | B65D 83/0454 221/133 |
| 2012/0083666 A1 * | 4/2012 | Waugh | ...................... | A61J 7/04 600/300 |
| 2013/0066463 A1 * | 3/2013 | Luoma | .................. | A61J 7/0084 700/232 |
| 2013/0175289 A1 * | 7/2013 | Sternberg | ............... | B65C 9/1869 221/70 |
| 2014/0114471 A1 * | 4/2014 | Kim | ...................... | A61J 7/0076 700/236 |
| 2014/0139998 A1 * | 5/2014 | Tasi | ........................ | G06F 1/20 361/679.48 |
| 2014/0346184 A1 * | 11/2014 | Bae | ....................... | A61J 7/0445 221/1 |
| 2016/0107820 A1 * | 4/2016 | MacVittie | ............... | A61J 7/049 221/13 |
| 2016/0128906 A1 * | 5/2016 | Baarman | ................. | A61J 7/0481 221/2 |
| 2016/0355322 A1 * | 12/2016 | Burton, Jr. | ............ | A61J 7/0481 |
| 2019/0031424 A1 * | 1/2019 | Nickerson | ............. | B65D 51/24 |
| 2019/0046412 A1 * | 2/2019 | Brady | .................... | A61J 7/0084 |
| 2019/0130078 A1 * | 5/2019 | Herbert | ................ | G16H 20/13 |
| 2019/0133886 A1 * | 5/2019 | Brecht | .................. | A61J 7/0481 |

FOREIGN PATENT DOCUMENTS

| | | | | |
|---|---|---|---|---|
| WO | | 2010105453 A1 | 9/2010 | |
| WO | WO-2016196982 A1 * | 12/2016 | ............ | A61J 7/0481 |

* cited by examiner

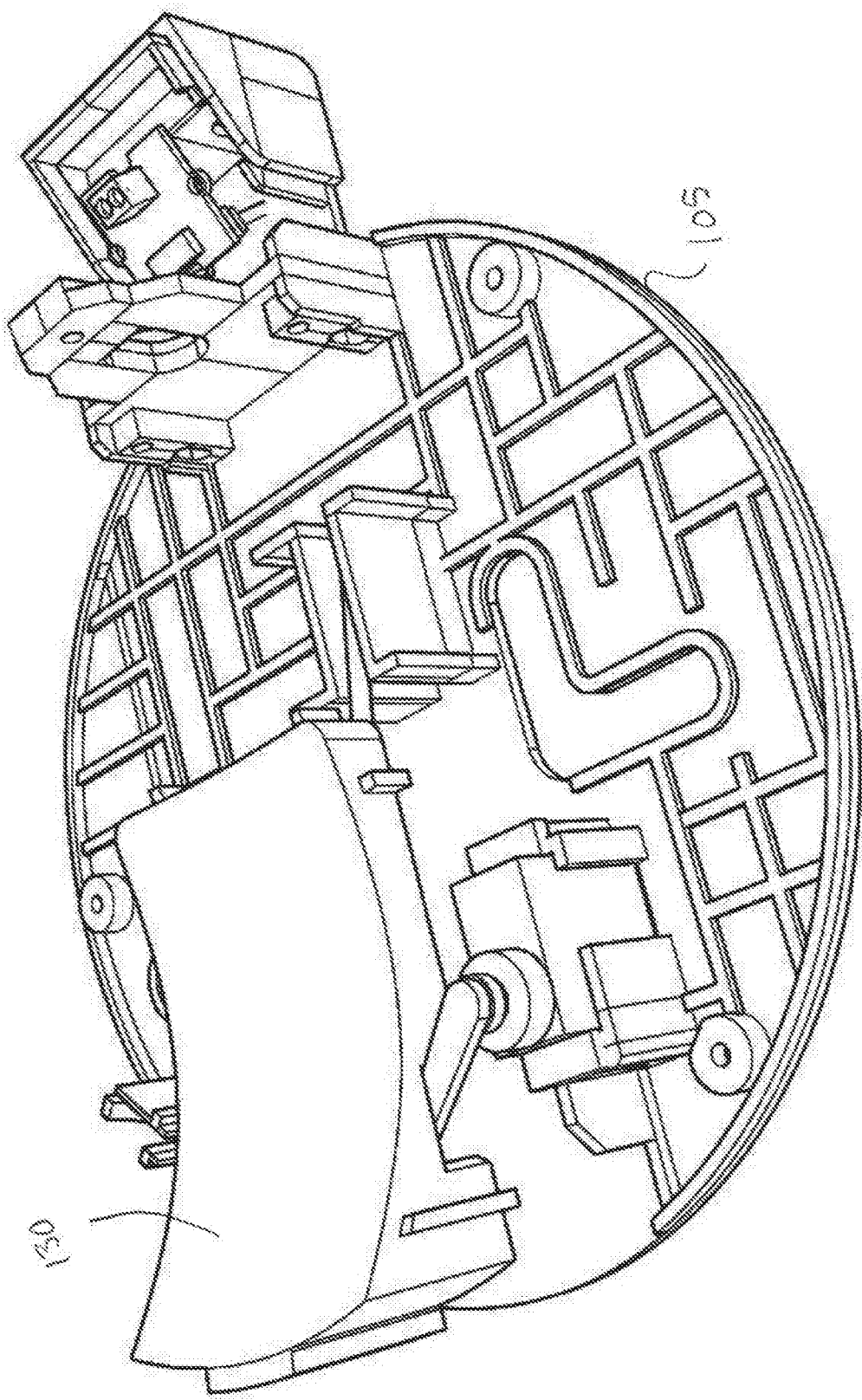

DISPENSER OF SUBSTANCE DOSES WITH DISH FOR COLLECTION THEREOF

TECHNICAL FIELD

The present disclosure relates to the facilitation of the taking of substances by users. More specifically, this disclosure relates to dispensing devices of such substances.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

The taking of substances (for example, medicines by patients) is a very common operation (especially for people that are no longer young). Generally, the medicines should be taken respecting corresponding dosages that specify the amount of each medicine and its frequency.

However, compliance with such dosages is not entirely easy. In fact, especially in case of very old patients or patients with mnemonic problems, it may be difficult to remember the taking times of the medicines. In addition, especially in case of very old patients or patients with physical problems, the opening of the packages of the medicines may be difficult (for example, when they are equipped with child safety systems). This may cause the missing taking of the medicines or their incorrect taking, with potential (even serious) risks for the health of the patients.

Dispensing devices (or simply dispensers) of medicines have been proposed to facilitate their taking. In their simplest form, such dispensers are provided with compartments to receive a series of doses of the medicines for a certain period, possibly with tags to indicate their taking times. More recently, automatic dispensers have also appeared, which allow (in addition to loading the doses of the medicines for a certain period) programming their taking times (for example, through a display and corresponding keys). Once each taking time is reached, such (automatic) dispensers provide a corresponding notice to remind the taking of the corresponding dose (for example, of acoustic type); in addition, the dispensers may also send corresponding messages to telephones of the patients. In response thereto, the patients may obtain the doses to be taken by acting on a suitable command of the dispenser. Some dispensers also allow accessing information about their conditions remotely (for example, via the Internet), in particular to detect any missing taking of the medicines; for example, this allows doctors of the patients to compensate for the missing taking of the medicines by adding recovery doses or by modifying their taking.

Generally, the dispensers are provided with a releasing slot of the medicines and with a mobile system (for example, a wheel) for bringing the medicine doses to the releasing slot. Whenever the patient is required to take a medicine dose (in response to the corresponding notice), the patient brings his/her dispenser, with the releasing slot facing downwards, over an open hand or over a table. At this point, the patient presses a corresponding button that causes the exit of the dose through the releasing slot and its fall by gravity (onto the hand of the patient or onto the table).

However, the release of the medicines from the dispenser may be quite difficult. Indeed, this requires the coordination of different movements. In particular, a hand is used to cause the release of the medicines from the dispenser; the other hand is instead used to receive the medicines that fall thereon or to grab them once fallen onto the table. These operations may not be not completely easy, especially in case of very old patients or patients with physical problems. This may cause the falling of the medicines, with further difficulties for their search and collection. In such a condition, it is very often difficult for the patient to find the fallen medicines so that they are generally lost. Consequently, the lost medicines are not taken by the patient (with the already highlighted possible risks for his/her health). The medicines that have been released by the dispenser but that have been lost might appear as taken by the patient to his/her doctor. Therefore, it is not possible to detect their missing taking to intervene for compensating it accordingly.

In addition, the loading of the medicines into the dispensers is quite uncomfortable (since the corresponding keys used to enter the taking times may be difficult to use). In addition, any medicines that are not taken (and that are therefore left in the dispenser) may create difficulties for a next loading of the dispenser (with the risk of possible mistakes caused by confusion with the medicines to be load).

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of providing a collection plate.

Particularly, an aspect provides a dispensing device for dispensing substances to be taken by a user, wherein the dispensing device comprises a plate having a collecting surface in a central zone thereof for collecting each dose of one or more substances released from compartments arranged in a peripheral zone of the plate.

A further aspect provides an assistance system comprising this dispensing device and a processing device.

A further aspect provides a processing device for use in this assistance system.

A further aspect provides a corresponding method.

A further aspect provides a computer program (software) for implement the method; a further aspect provides a corresponding software program product.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes—such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly:

Each of FIGS. 6A-6C shows a perspective view of the dispenser in FIGS. 1 and 2 with the pushbutton located in a different position relative to the unloading opening.

Each of FIGS. 7A and 7B shows a perspective view of the pushbutton mounted to the base of the dispenser. FIG. 7A shows the pushbutton locked in the position that blocks the unloading opening (shown in FIG. 6A).

DETAILED DESCRIPTION

Figure 1:
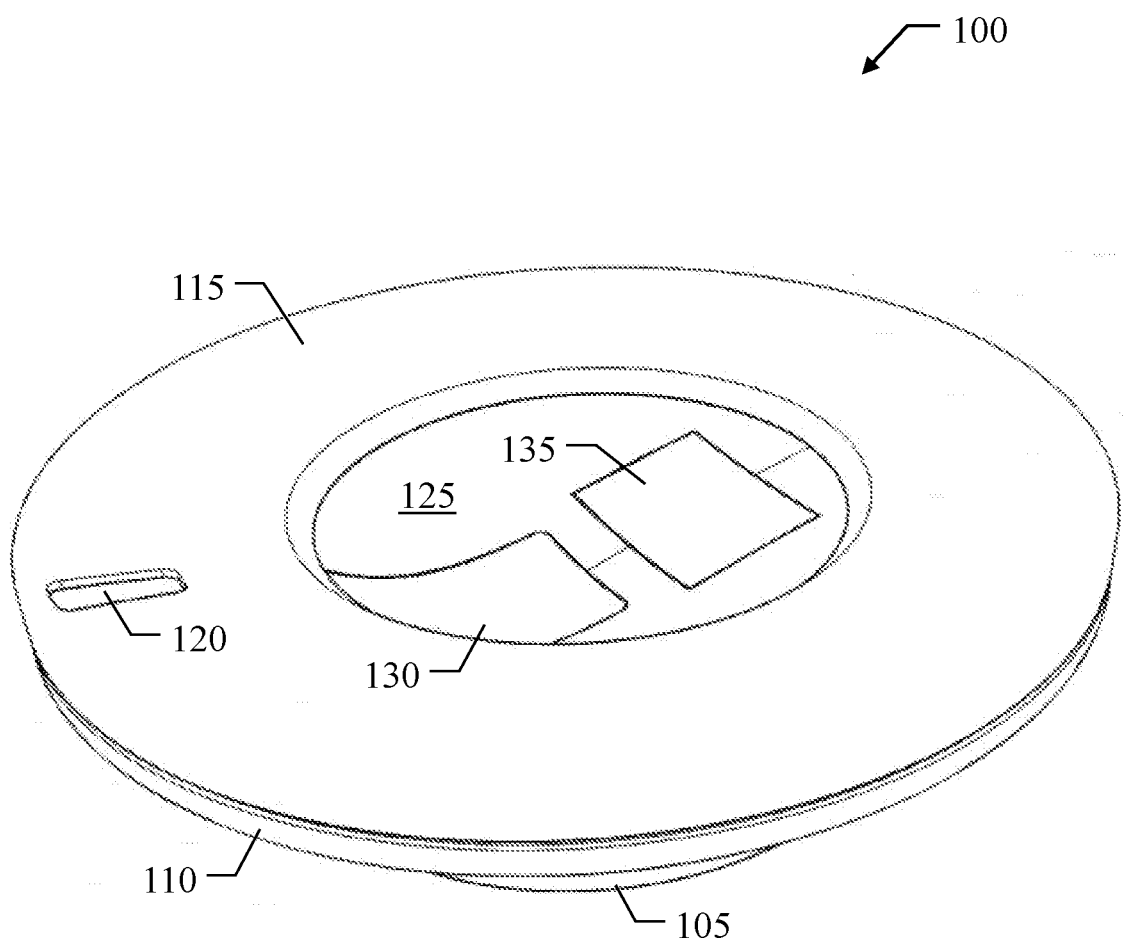
FIG. 1 shows a schematic representation of a dispenser according to an embodiment of the present disclosure.

With reference in particular to FIG. 1, a schematic representation is shown of a dispenser (device) 100 according to an embodiment of the present disclosure.

The dispenser 100 is used to dispense substances (for example, medicines) to be taken by a user (for example, a patient like an elderly person). The dispenser 100 comprises a shell with general disk-like shape (for example, made of plastic with a height of 5-10 cm and a diameter of 20-30 cm). The shell comprises a narrow base 105 (for example, with a height of 2-4 cm and a diameter of 10-15 cm), which houses various mechanical/electronic components (such as a controller, an engine of a wheel, a loudspeaker, a position sensor of the wheel, an end-of-stroke switch of a pushbutton), a (rechargeable) battery for supplying the dispenser 100 and a corresponding electric socket (not shown in the figure).

The base 105 is surmounted by a plate 110 (for example, with a height of 2-4 cm), which extends throughout the entire width of the shell. A peripheral area of the plate 110 (for example, with a width of 4-6 cm) is covered by a lid 115 integral thereto, which closes (on top) a plurality of compartments, for example, 20-40 (not shown in the figure); each compartment is used to contain a dose of one or more substances to be taken by the patient (for example, one or more pills). The lid 115 is provided with a loading opening 120 (for example, a slot extending radially with a width of 1-2 cm and a length of 2-3 cm); the loading opening 120 is used to load the pills into the underlying compartments.

The plate 110 is provided with a collecting surface 125 in a central area thereof (within its peripheral area wherein the compartments are located under the lid 115). The collecting surface 125 houses a pushbutton 130, which is relatively large in size to facilitate its use (for example, 3-5 cm×6-8 cm); as described in detail in the following, the pushbutton 130 is used to release each dose from the corresponding compartment towards the central area of the plate 110. In addition, the collecting surface 125 houses a display 135, which is of the electronic paper (e-paper) type to limit the consumption of electric energy and with relatively large dimensions (for example, 3-5 cm×5-7 cm) to facilitate the reading; the display 135 is used to provide information to the patient with respect to the doses to be taken.

In the solution according to an embodiment of the present disclosure, each dose released by the corresponding compartment (by acting on the pushbutton 130) is collected onto the collecting surface 125.

This greatly facilitates the release of the doses. Indeed, in this way the operation is very simple and natural, so that it becomes easy even for very old patients or patients with physical problems. The solution described above avoids (or at least substantially reduces) the risk that doses might fall and are therefore lost. Consequently, it is much more likely that the released doses are actually taken by the patient (thereby substantially reducing the risks for his/her health).

Preferably, the collecting surface 125 is concave (for example, with a ratio between its maximum depth (at the center) and its diameter equal to 0.05-0.2, preferably 0.07-0.15 and even more preferably 0.08-0.12, such as equal to 0.1); this further simplifies the release of the doses, thereby making it safer their collection.

Figure 2:
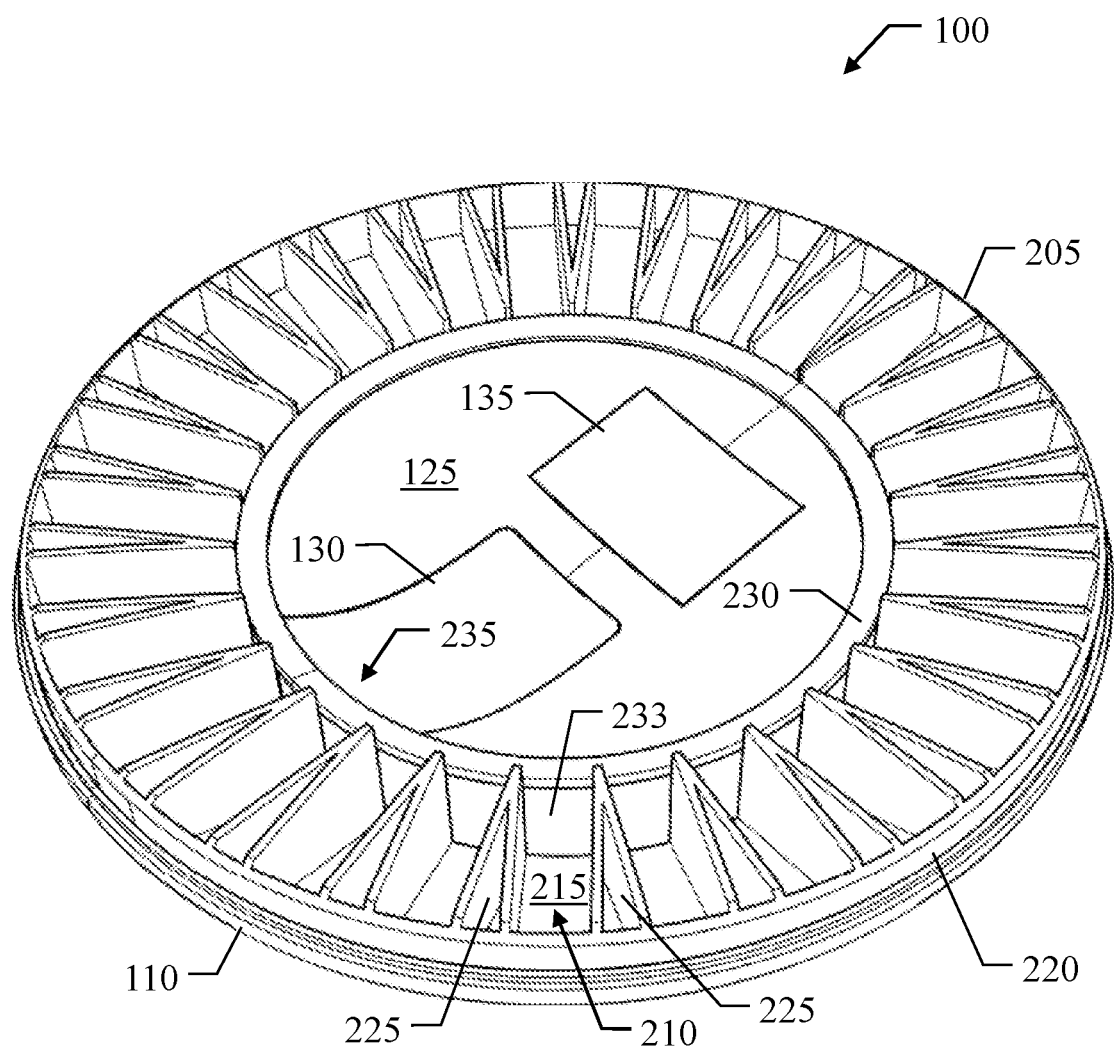
FIG. 2 shows a partially cut away view of the dispenser according to an embodiment of the present disclosure.

With reference now to FIG. 2, a partially cut away view is shown of the dispenser 100 according to an embodiment of the present disclosure.

Figure 9:
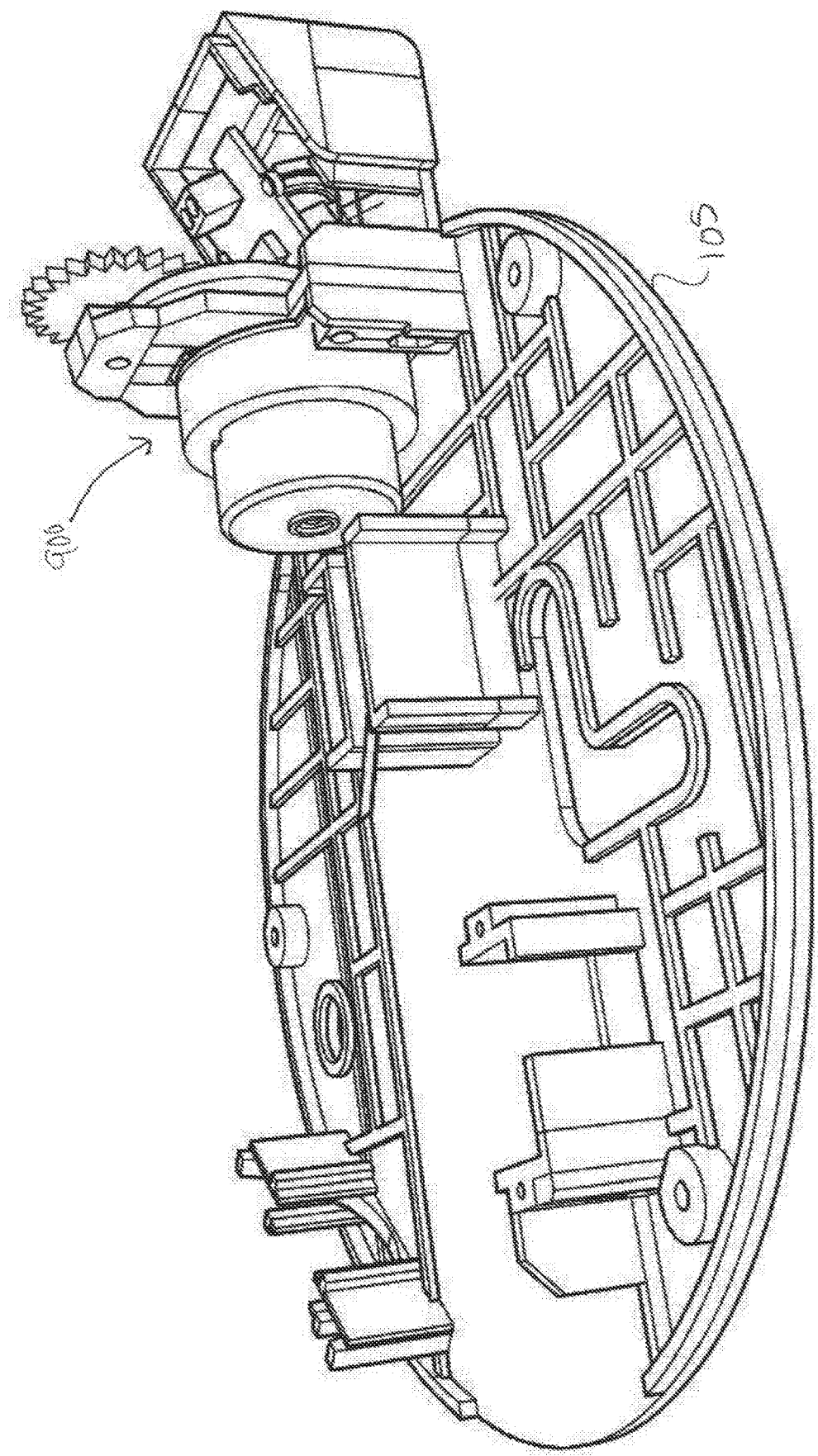
FIG. 9 shows a perspective view a motor mounted to the base of the dispenser shown in FIGS. 1 and 2.
Figure 10:
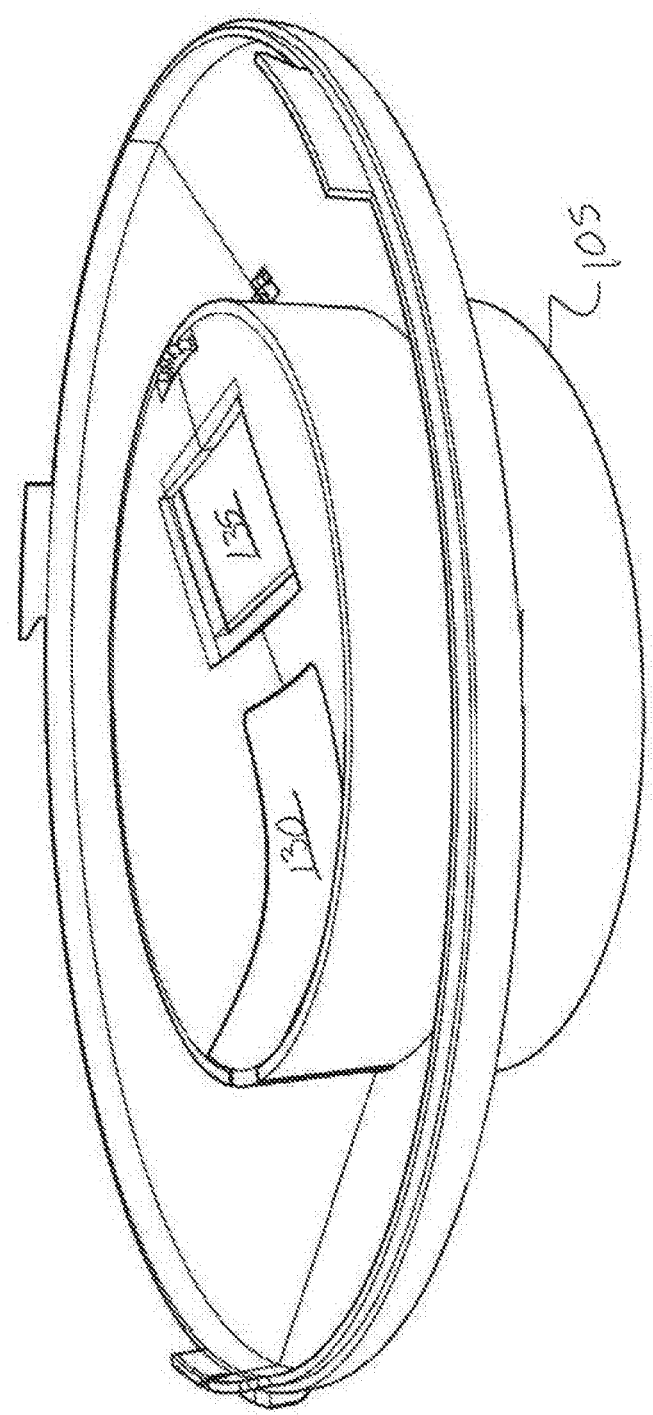
FIG. 10 shows a perspective view of the base of the dispenser shown in FIGS. 1 and 2.

The dispenser 100 comprises a wheel 205 located in the peripheral area of the plate 110 (covered by the lid, not shown in the figure); an electric motor not visible in the figure (for example, a stepper motor 900 shown in FIG. 9) may rotate the wheel 205 (for example, clockwise). The wheel 205 houses the compartments for the doses of the medicines, denoted with the reference 210, which are evenly distributed along it. In particular, the wheel 205 comprises a (flat) ring 215 slightly sloping towards the central area of the plate 110 (for example, at an angle of 5-15°); a (closing) wall 220 extends transversely to the ring 215 (upwardly in the figure) from an outer edge thereof (for example, with a height of 2-4 cm). A series of separators 225 arranged radially (uniformly along the ring 215) also extend transversely to the ring 215 (upwardly in the figure) to define a corresponding compartment 210 between each pair thereof being adjacent; each separator 225 is formed by two septum converging towards the central area of the plate 110 (so as to confer a V-like section to the separator 225), with each pair of facing septum (of two adjacent separators 225 defining a corresponding compartment 210) that are parallel. The inclination of the ring 215 facilitates the fall of the doses released from the compartments 210 onto the collecting surface 125 by gravity; moreover, the constant width of the compartments 210 prevents (or at least makes it much less likely) that the doses to be released got stuck within them. In both cases, this facilitates the collection of the doses onto the plate 110. A ring 230 joins the free ends of the separators 225; the ring 230 is arranged near an upper end of the separators 225 (distal from the ring 215), leaning on a free edge of plate 110; in this way, the ring 230 (spaced apart from the ring 215) leaves the compartments 210 open towards the collecting surface 125; the compartments 210 are instead closed towards the collecting surface 125 by a lateral surface 233 of the plate 110. The lateral surface 233 is provided with a releasing opening 235 (for example, with a height of 1-2 cm and a width of 1-3 cm) in correspondence to the button 130, staggered by half the width of each compartment 210 with respect to the loading opening (not shown in the figure); the releasing opening 235 is used to release the doses from each compartment 210 arranged in correspondence therewith (towards the collecting surface 125).

In a rest condition, the wheel 205 is arranged so that a compartment 210 is in front of the releasing opening 235; in this condition, a separator 225 is located under the loading opening, so as to prevent any insertion/removal of medicines through it. At the same time, a spring (not shown in the figure) keeps the pushbutton 130 flush with the collecting surface 125 (so as to leave it completely free); in this condition, the pushbutton 130 is in front of the releasing opening 235 so as to obstruct it, i.e., to close it (in order to avoid the release of any dose contained in the compartment 210 in front of it). In addition, the pushbutton 130 is locked (for example, through a latch not shown in the figure) so as to prevent its pressure with the release of such dose when not appropriate.

When the medicines are to be loaded into the dispenser 100, the motor moves the wheel 205 so as to bring each compartment 210 that is free (i.e., empty) under the loading opening (to allow the corresponding dose to be inserted through it). When the medicines are to be released by the dispenser 100, the motor moves the wheel so as to bring each compartment 210 containing the dose to be released in front of the unloading opening 235 (with a separator 225 thereof under the loading opening). At this point, the pushbutton 130 is unlocked; as soon as the pushbutton 130 is pressed (in opposition to its spring) it retracts into the collecting surface 125 so as to clear, i.e., open, the release slot 235. The dose contained in the compartment 210 in front of the releasing opening 235 therefore falls by gravity onto the collecting surface 125.

Figure 3:
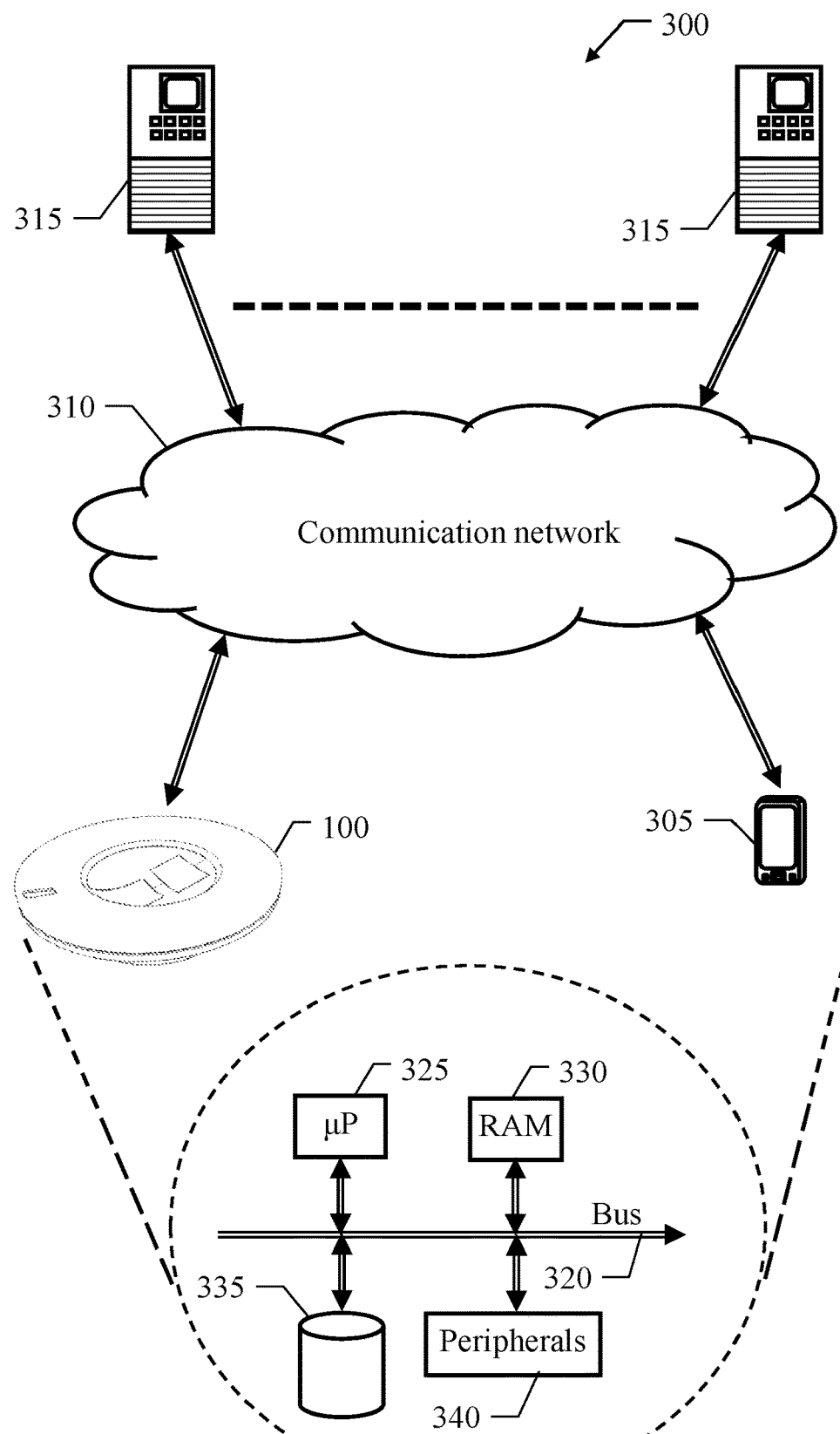
FIG. 3 shows a schematic block diagram of an assistance system according to an embodiment of the present disclosure.

With reference now to FIG. 3, a schematic block diagram is shown of an assistance system 300 according to an embodiment of the present disclosure.

The assistance system 300 is used to facilitate the taking of the medicines by the patient. For this purpose, the assistance system 300 comprises the dispenser 100 and a smartphone 305; the smartphone 305 is normally in the possession of the patient (for the use of the dispenser 100) while it may be provided to an operator of the dispenser 100 (for example, a relative of the patient) for its loading/unloading. The dispenser 100 and the smartphone 305 may communicate to each other via a communication network 310 (for example, in a secure form on a local network). The same communication network 310 is also used by the dispenser 100 and the smartphone 305 to communicate with other computers 315 (for example, always in a secure form in the Internet); for example, such computers 315 may comprise a smartphone of one or more relatives of the patient, a computer (for example, a PC) of a doctor of the patient, a server computer of one or more producers of the medicines.

Each computing machine of the assistance system 100 (i.e., dispenser, PC and server) comprises several units that are connected in parallel to a communication bus 320 (with a structure that is suitably scaled according to the actual function of the computing machine). In detail, one or more processors 325 control operation of the computing machine and a volatile memory (RAM) 330 is used as a working memory by the processors 330. The computing machine is provided with a mass-memory 335 for storing information to be preserved even when a power supply is off; for example, the mass-memory 335 is a flash $E^2PROM$ in the dispenser and in the smartphones, a hard disk in the PCs and strings of disks in a center (server farm) that implements the servers therefor. Moreover, the computing machine comprises different peripherals, or Input/Output (I/O) units 340; for example, the peripherals 340 comprise controllers of the display, of the loudspeaker, of the motor, of the position sensor of the wheel, of the end-of-stroke switch of the pushbutton and a network card of Wi-fi type for the dispenser, a controller of a touch-screen, a network card of Wi-Fi type and a transceiver of 3G type for the smartphone, controllers of connection ports for monitor, keyboard and mouse, controllers for reading/writing removable storage units (like optical disks) and a network card of Wi-Fi type for the PC, and a network card of Ethernet type and controllers for reading/writing removable storage units (like optical disks) of a console of the server farm for the server.

Figure 4:
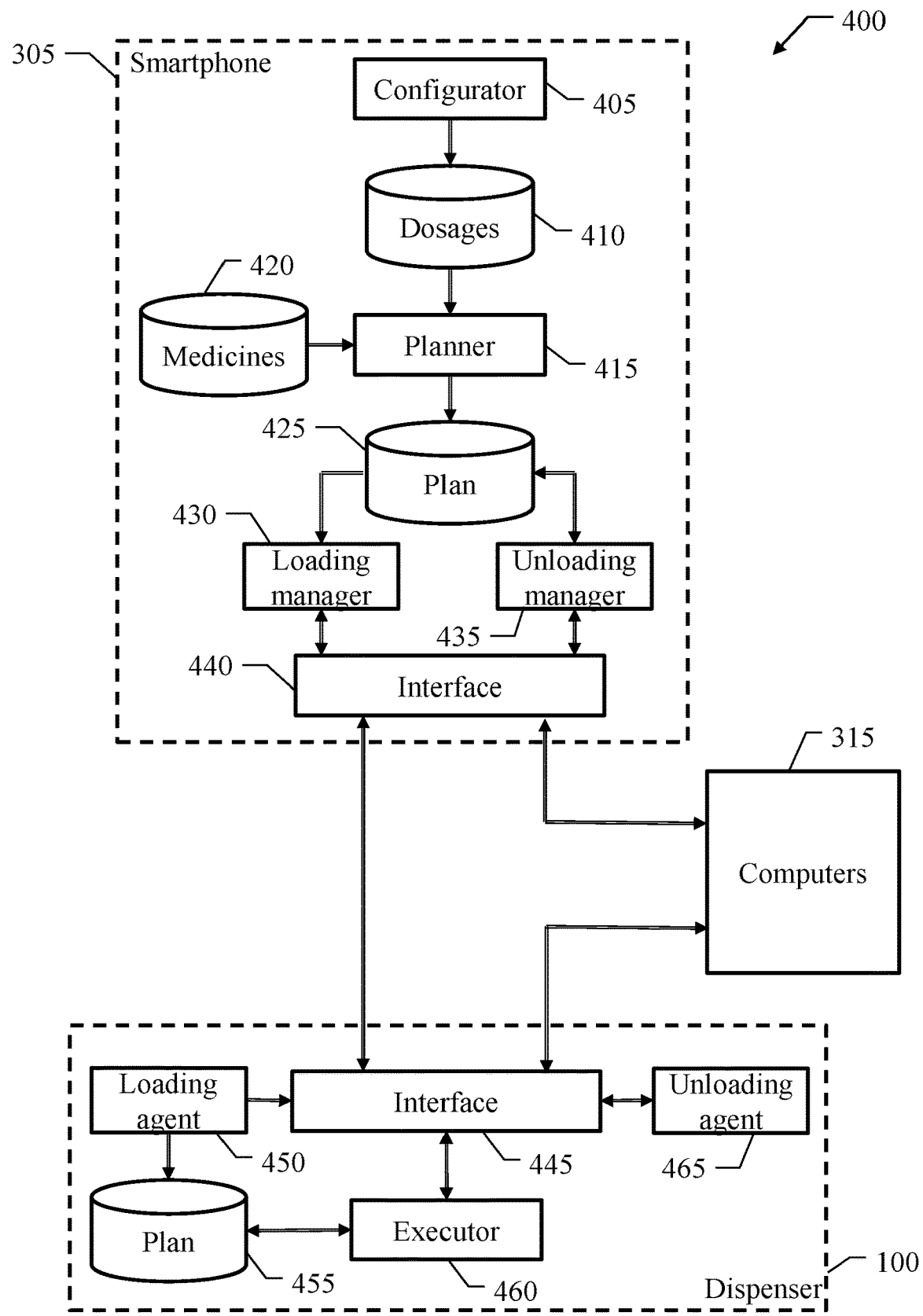
FIG. 4 shows the main software components that may be used to implement the solution according to an embodiment of the present disclosure.

With reference now to FIG. 4, the main software components are shown that may be used to implement the solution according to an embodiment of the present disclosure.

Particularly, all the software components (programs and data) are denoted as a whole with the reference 400. The software components 400 are typically stored in the mass memory and loaded (at least partially) into the working memory of the dispenser 100 and of the smartphone 305 (of the patient) when the programs are running. The programs are initially installed into the mass memory, for example, from removable storage units or from the communication network. In this respect, each program may be a module, segment or portion of code, which comprises one or more executable instructions for implementing the specified logical function.

Considering in particular the smartphone 305, a mobile application (app) for managing the dispenser 100 is loaded therein. Such mobile application comprises a configurator 405 which is used to create a (new) (taking) dosage of one or more medicines for the patient; the dosage is defined by rules that specify, for each medicine to be taken, the amount (for example, number of pills of a given weight), frequency (for example, every number of hours, at meals), and maximum taking delay (for example, number of hours). The configurator 405 controls (in write mode) a dosage file 410 wherein it is stored. A planner 415 is used to create a (new) taking plan of these medicines for the patient. For this purpose, the planner 415 accesses (in read mode) the dosage file 410 and a medicine repository 420; the medicine repository 420 contains taking information of the medicines (for example, taking at full/empty stomach, effects of the medicine on drive ability). The taking plan comprises an entry for each taking of the medicines (over a period depending on the number of compartments of the dispenser); the entry comprises an indication of the taking time, a corresponding taking dose (for example, number of pills of one or more medicines), maximum taking delay and any corresponding taking information. The planner 420 controls (in write mode) a taking plan repository 425; the taking plan repository stores the (new) taking plan still to be executed and logs the (previous) taking plans already executed. A loading manager 430 controls the loading of the dispenser 100 (remotely); for this purpose, the loading manager 430 accesses (in read mode) the taking plan repository 425. An unloading manager 435 instead controls the unloading of the dispenser 100 (remotely); for this purpose, the unloading manager 435 accesses (in read/write mode) the taking plan repository 425. In addition, both the loading manager 430 and the unloading manager 435 exploits a communication interface 440; the communication interface 440 is used to communicate with the dispenser 100 and possibly with the computers 315.

Passing to the dispenser 100, a communication interface 445 is likewise used to communicate with the smartphone 305 and possibly with the computers 315. The communication interface 445 interacts with a loading agent 450, which controls the loading of the dispenser 100 (locally); the loading agent 450 controls (in write mode) a taking plan file 455 wherein a local copy of a (current) taking plan is stored. An executor 460 is used to control the taking of the medicines according to the taking plan; for this purpose, the executor 460 accesses (in read/write mode) the taking plan file 455 and interacts with the communication interface 445. An unloading agent 465 instead controls the unloading of the dispenser 100 (locally); for this purpose, the unloading agent 465 interacts with the communication interface 445.

Figure 5A:
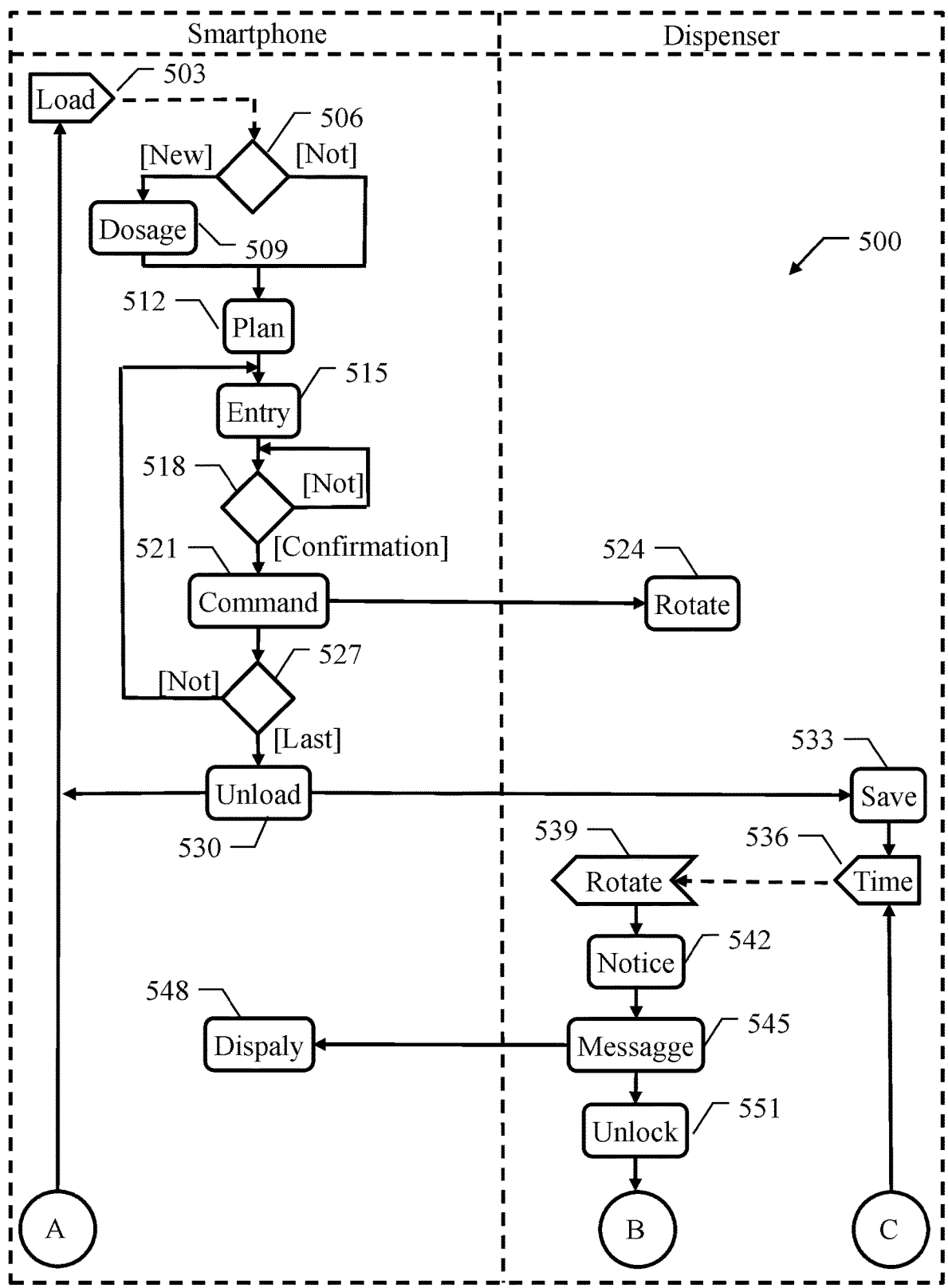
FIG. 5A-FIG. 5B show an activity diagram describing the flow of activities relating to an implementation of the solution according to an embodiment of the present disclosure.
Figure 5B:
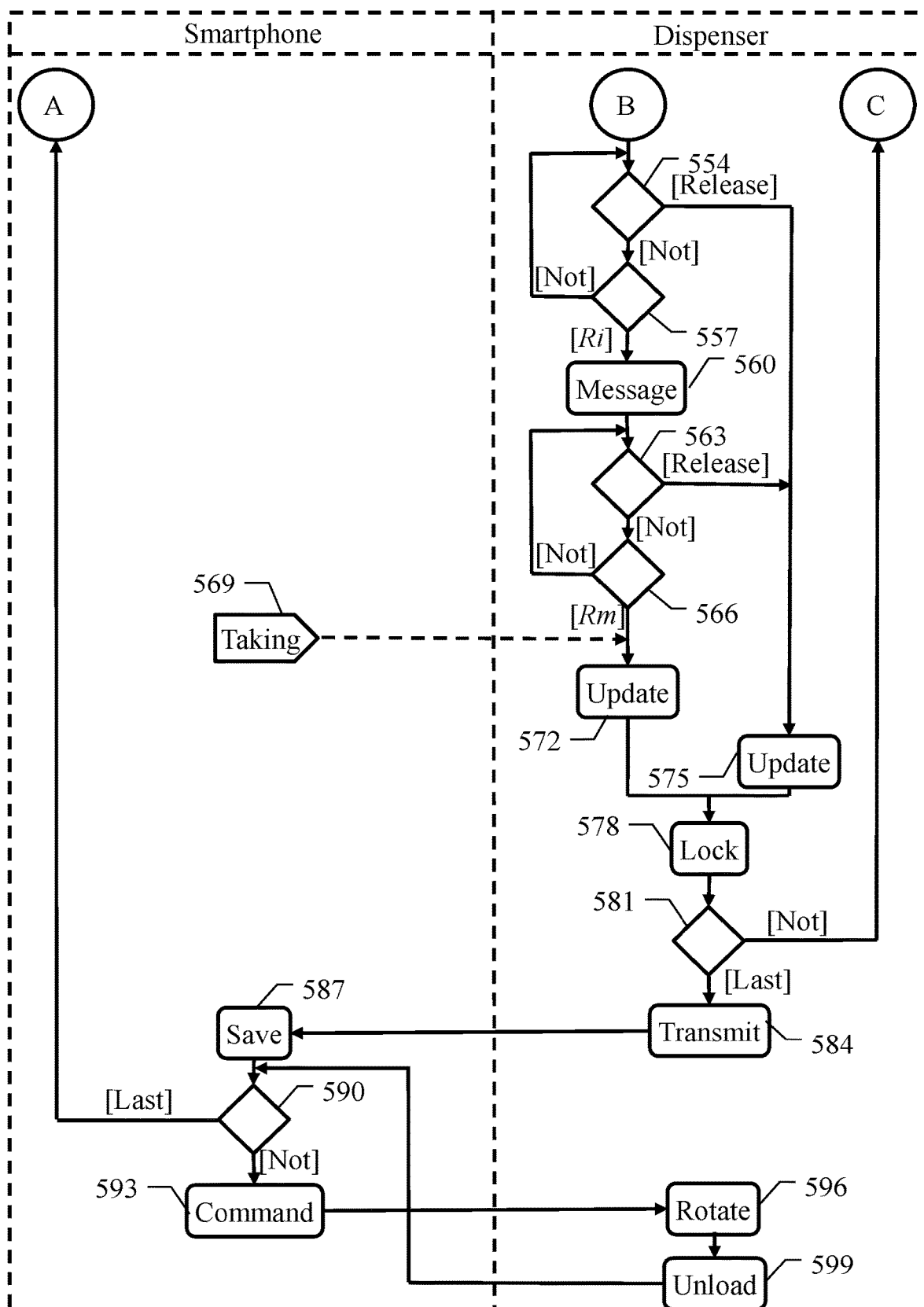
Figure 6A:
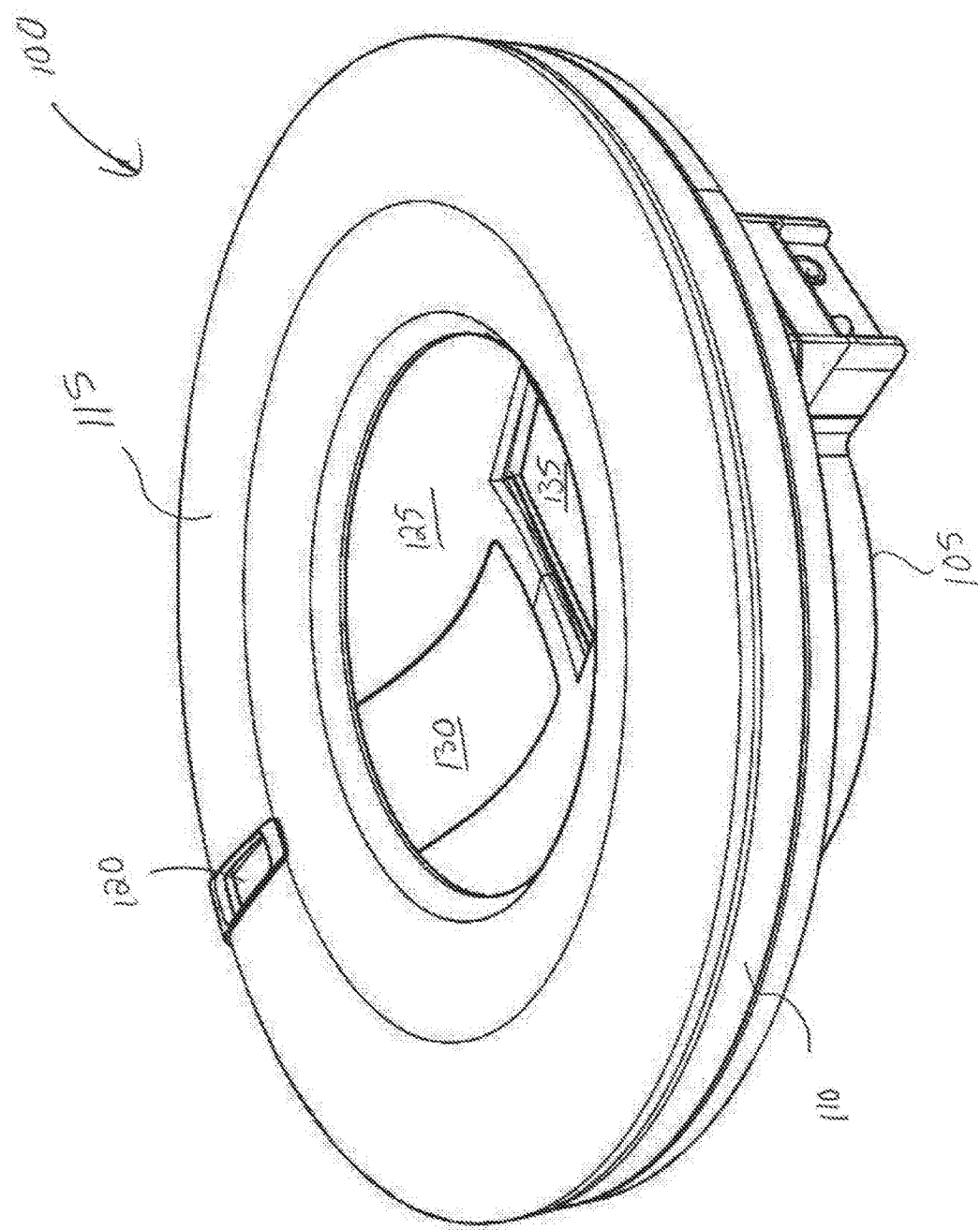
FIG. 6A shows the pushbutton in a position that blocks the unloading opening.
Figure 6B:
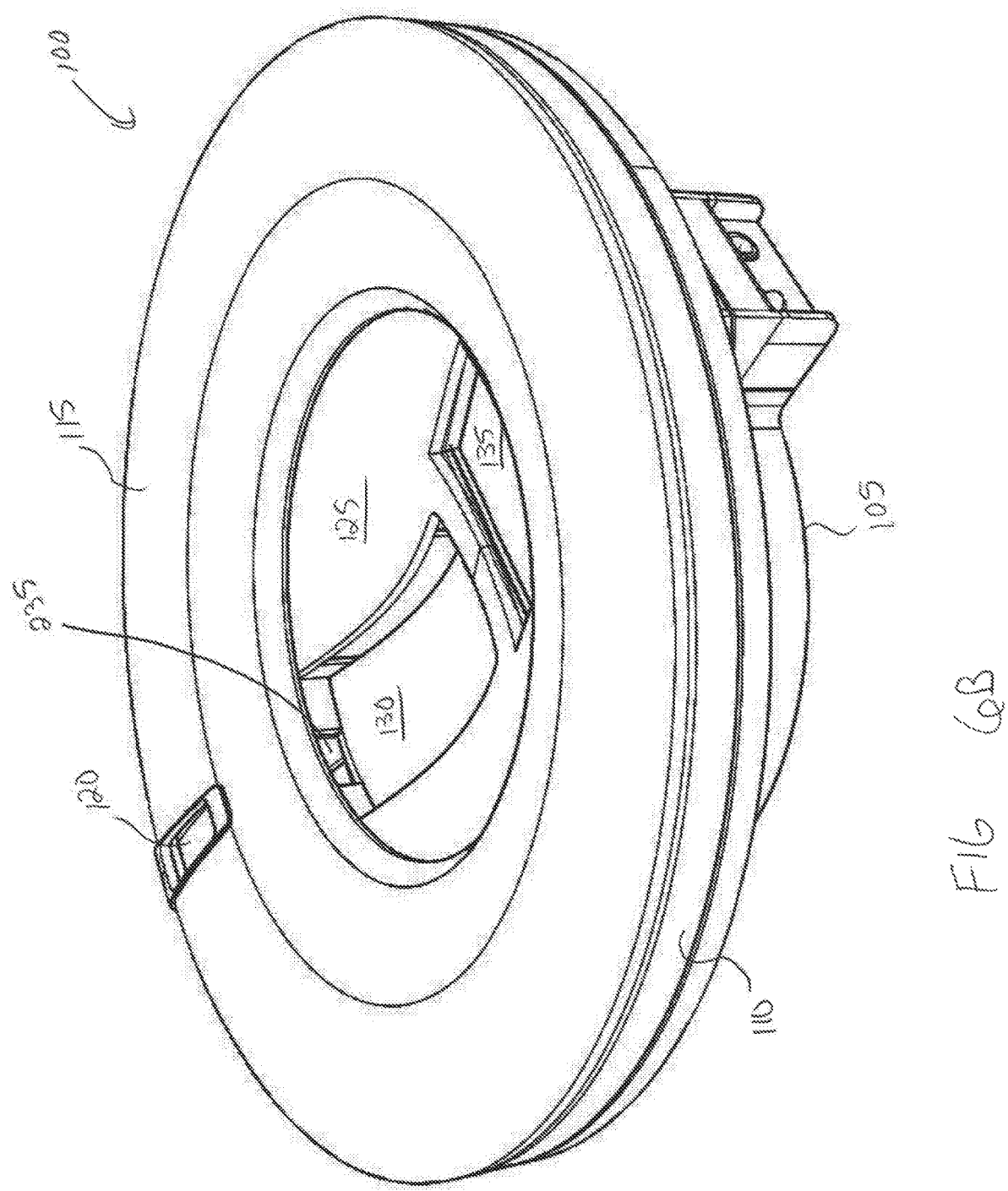
FIG. 6B shows the pushbutton in a position between those shown in FIGS. 6A and 6C.
Figure 6C:
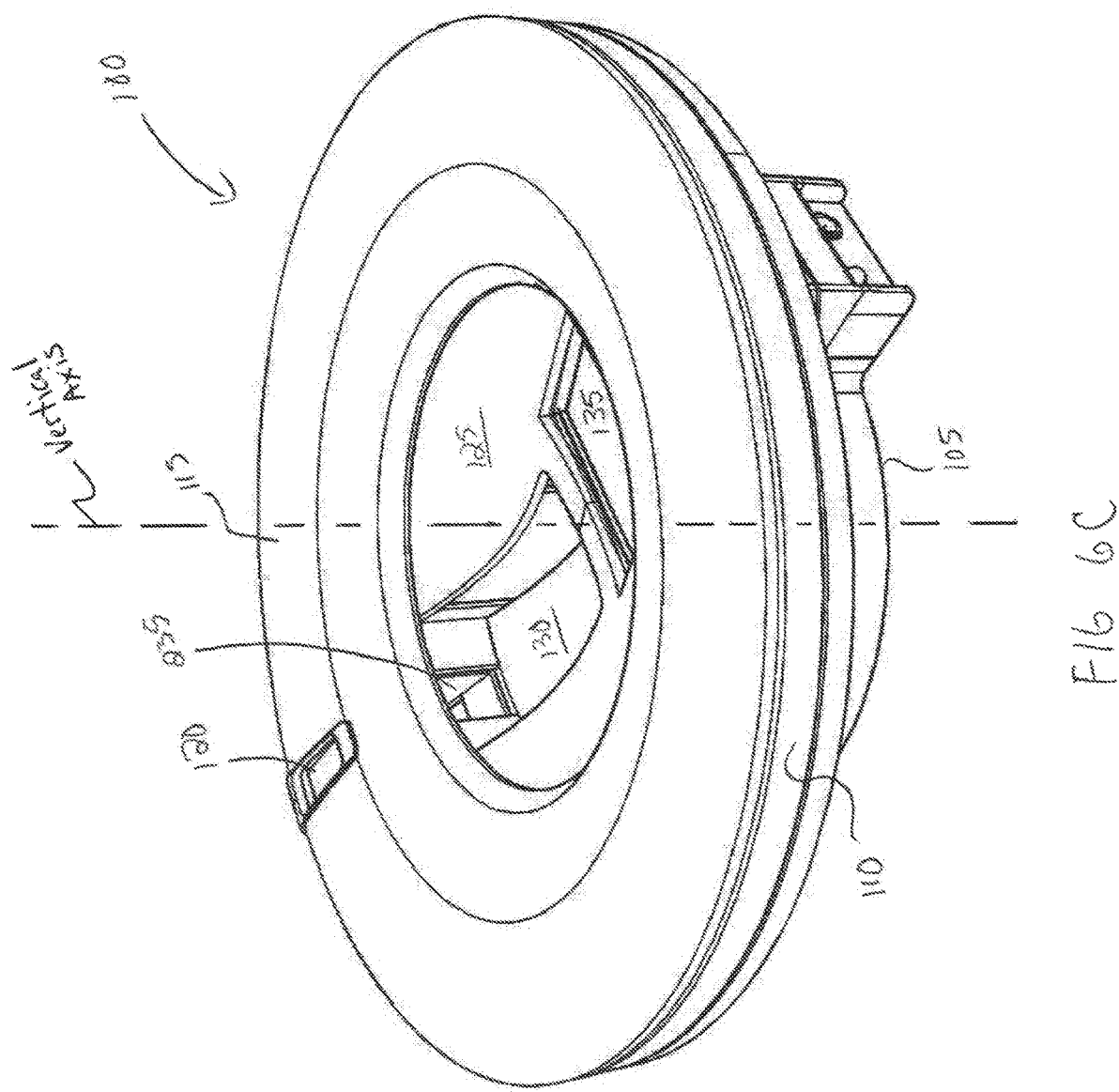
FIG. 6C shows the pushbutton in a position that does not block the unloading opening.
Figure 7B:
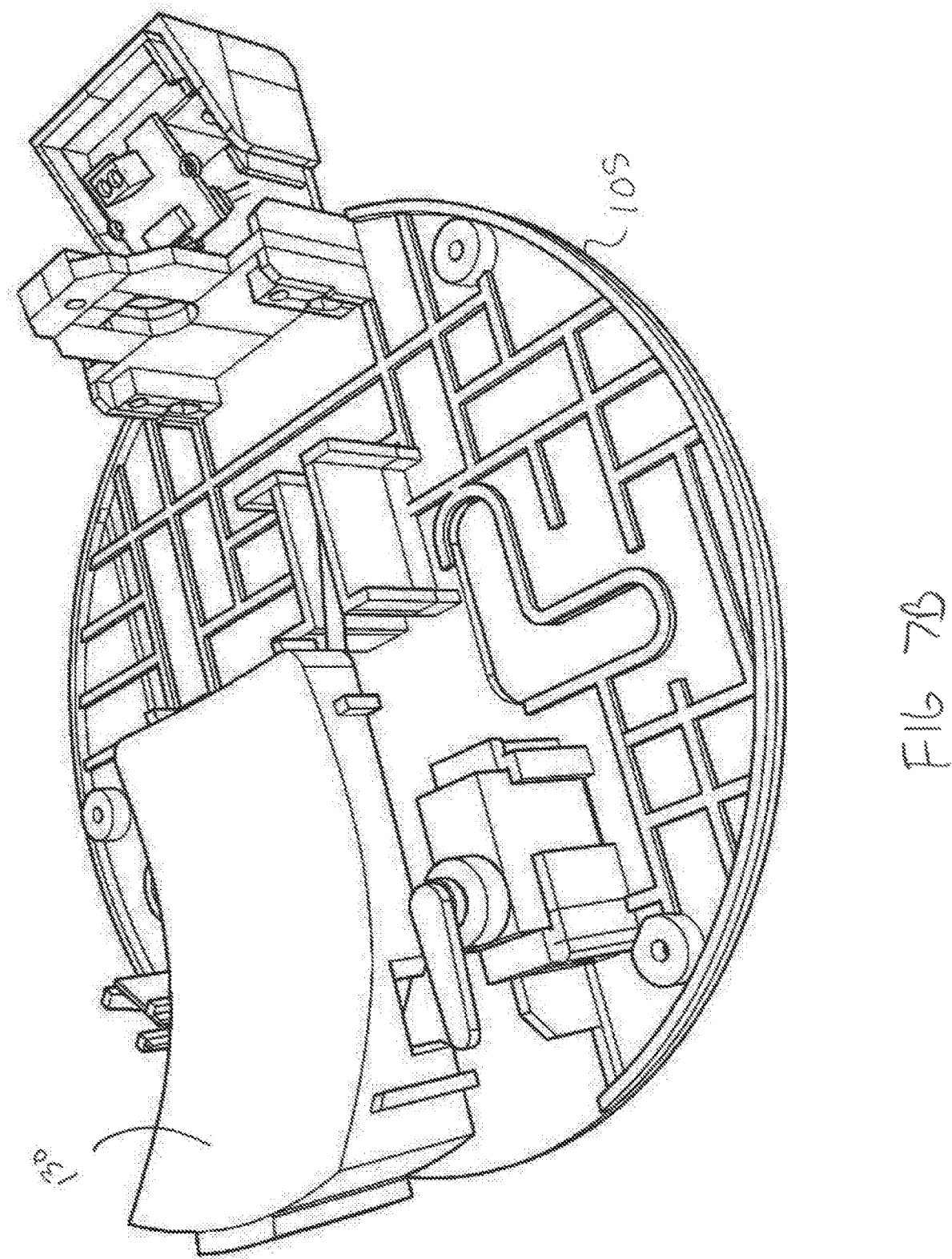
FIG. 7B shows the pushbutton unlocked in the position that blocks the unloading opening, and ready to be moved to unblock the unloading opening (shown in FIGS. 6B and 6C).
Figure 8:
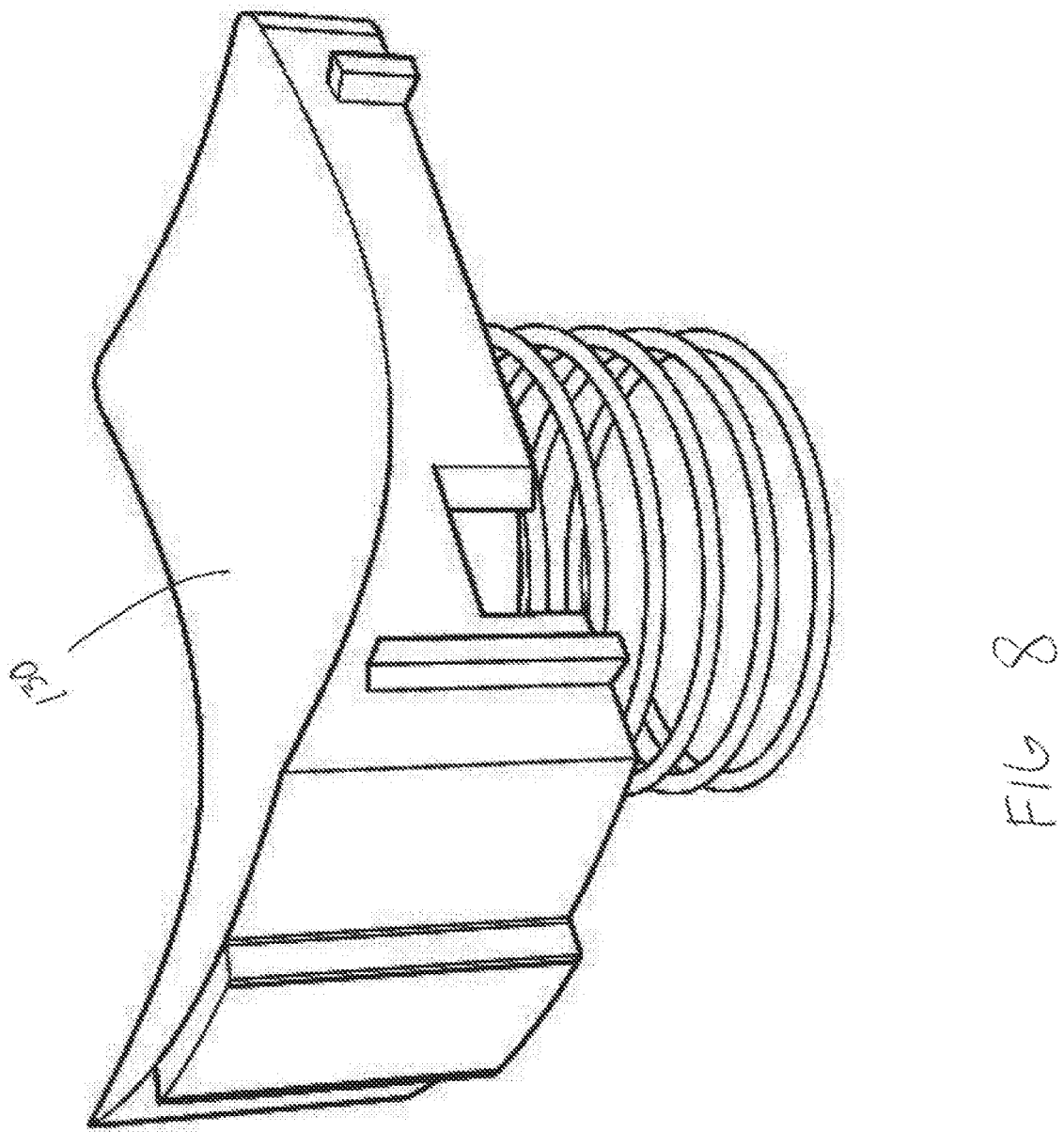
FIG. 8 shows a perspective view of the pushbutton mounted to a spring that urges the pushbutton in the position that blocks the unloading opening (shown in FIG. 6A).

With reference now to FIG. 5A-FIG. 5B, an activity diagram is shown describing the flow of activities relating to an implementation of the solution according to an embodiment of the present disclosure.

In this respect, each block may correspond to one or more executable instructions for implementing the specified logical function on the dispenser 100 or on the smartphone 305 (of the patient). Particularly, the diagram represents an exemplary control process of the dispenser with a method 500.

Starting from the swim-lane of the smartphone, the process passes from block 503 to block 506 when the operator requests to load the dispenser (for example, by selecting a corresponding command of the mobile application for managing the dispenser). In response thereto, the flow of activity branches according to the type of dosage. If the operator selects the creation of a new dosage, this happens at block 509 (for example, with the operator that enters the corresponding information, i.e., amount, frequency, and maximum taking delay for each medicine via a graphical interface of the configurator or with the configurator that receives its definition from the computer of the doctor of the patient through the communication interface); in any case, the configurator saves the (new) dosage into the dosage file (by replacing any previous version thereof). The process then continues to block 512; the same point is also reached directly from the block 506 if the operator selects the already existing dosage. In any case, at this point the planner creates the (new) taking plan corresponding to the dosage. For this purpose, the planner resolves any possible parameter of the dosage (for example, meal times) based on information entered by the operator manually or retrieved from corresponding configuration variables. The planner then adds a new entry to the taking plan (initially empty) for each next dose of the medicines to be taken with the indication of the dose itself, its taking time and its maximum taking delay (according to the dosage) and of the possible taking information (extracted from the medicine file, for example, downloaded from Internet sites implemented by the servers of the corresponding producers); this operation is repeated at most up to a number of doses equal to the number of the compartments of the dispenser (indicated in a corresponding configuration variable) less one, in order to always leave an empty compartment in correspondence to the loading opening for avoiding any risk of insertion/removal of medicines through it. The planner then adds the taking plan to the taking plan repository.

At this point, a loading cycle of the dispenser is performed. The loading cycle begins at block 515 with the loading manager that extracts (from the taking plan file) the content of a (current) entry of the (new) taking plan, starting with the first one, and displays a load notice of the corresponding dose on the screen of the smartphone. The loading manager then enters a waiting condition at block 518 for a confirmation of the loading of the dose into the (free) compartment under the loading opening by the operator (for example, provided by the operator responding to a corresponding request of the mobile application for managing the dispenser). As soon as the loading manager receives the confirmation of loading, the process continues to block 521, wherein the loading manager sends a rotation command to the dispenser. In response thereto, in the swim-lane of the dispenser the loading agent at block 524 moves the wheel (via a controller of the motor) bringing a new free compartment under the loading opening. At the same time, in the swim-lane of the smartphone the process passes from block 521 to block 527; at this point, a test is executed wherein the loading manager verifies whether a last entry of the taking plan has been processed. If not, the flow of activities returns to the block 515 to repeat the same operations for a new entry of the taking plan. Conversely, as soon as all the entries of the taking plan have been processed, the loading cycle is completed by descending into block 530, wherein the loading manager downloads the taking plan to the dispenser. The process then returns to the block 503, waiting for a next request of loading the dispenser.

At the same time, passing to the swim-lane of the dispenser, the loading manager at block 533 receives the taking plan and it saves it into the corresponding file (replacing a possible previous version thereof). The flow of activities then descends to block 536 waiting for the taking time of a current entry of the taking plan (starting from the first one). As soon as this taking time is reached, the executor at block 539 moves the wheel (via the controller of the motor) to bring the compartment containing the corresponding dose (according to the taking plan) in front of the releasing opening. Continuing to block 542, the executor commands the loudspeaker (via a controller thereof) to output an acoustic notice and commands the display (via a controller thereof) to display a taking notice; for example, the taking notice indicates the dose and any possible taking information (extracted from the taking plan). Continuing to block 545, the executor transmits (via the communication interface) a similar taking notice to the smartphone. In response thereto, this taking notice is displayed onto the screen of the smartphone at block 548 in its swim-lane (for example, as a notification of the mobile application for managing the dispenser). At the same time, in the swim-lane of the dispenser the process passes from block 545 to block 551 wherein the executor unlocks the pushbutton (via a controller thereof). At this point, the patient is informed that it is time to take a dose of the medicines, so that s/he should press the pushbutton to open the releasing opening thereby causing the dose to fall onto the collecting surface. A verification cycle of the release of the dose is then performed. The verification cycle of the release of the dose begins at block 554, wherein the executor verifies whether the dose has been released from the corresponding compartment (as detected by the controller of the pushbutton via its end-of-stroke sensor). If not, the performer verifies at block 557 whether an initial delay (Ri) has elapsed since the display of the taking notice; the initial delay is always lower than the maximum taking delay (Rm) of the dose (extracted from the taking plan), for example, equal to a percentage thereof (such as Ri=0.3-0.5·Rm). If the initial delay has not elapsed yet, the process returns to the block 554 to repeat the same operations (periodically issuing an additional acoustic notice). On the contrary, as soon as the initial delay is elapsed (without the release of the dose) the flow of activity descends to block 560, wherein the executor transmits (via the communication interface) a notice of missing taking of the dose (for example, an SMS) to the smartphones of the relatives of the patient; this allows the relatives of the patient to intervene promptly (for example, by calling the patient or by going to his/her home). Continuing to block 563, the executor again verifies whether the dose has been released from the corresponding compartment. If not, the executor now verifies at block 566 whether the maximum delay has elapsed since the display of the taking notice. If the maximum delay has not elapsed yet, the process returns to the block 563 to repeat the same operations (periodically issuing a further acoustic notice). On the contrary, as soon as the maximum delay has elapsed (without the releasing of the dose) the release verification cycle is terminated.

The same point is also reached from block 569 in the swim-lane of the smartphone when the patient, in response to the taking notice, confirms the taking of an alternative dose of the same medicines (for example, by responding to the taking notice through a special command of the mobile application for managing the dispenser). In response thereto, the smartphone transmits a confirmation of alternative taking to the dispenser (for example, a corresponding message). In this way, it is also possible to handle situations wherein the patient does not have the dispenser available (for example, because s/he left by leaving it at home) but s/he is still able to take the medicines (for example, by a package thereof being bring with him/her).

In both cases, the process continues to block 572 in the swim-lane of the dispenser from the block 566 or the block 569. At this point, the executor updates the taking plan by adding a flag of missing release of the dose; in addition, if the corresponding alternative dose has been taken by the patient (i.e., the confirmation of alternative taking has been received), the executor updates the taking plan by also adding a flag of alternative taking, for example, comprising the transmission time of the confirmation of alternative taking (and hence of the presumed taking of the alternative dose). Returning to the block 554 and to the block 563, if the dose has been released, the process instead continues to block 575, wherein the executor updates the taking plan by adding the time of the releasing of the dose (and hence of its presumed taking). The flow of activity merges at block 578 from the block 572 or from the block 575. At this point, the executor locks the pushbutton (via its controller). A test is then performed at block 581, wherein the executor verifies whether a last record of the taking plan has been processed. If not, the process returns to the block 536 waiting for the taking time for a next entry of the taking plan.

Conversely, as soon as all the entries of the taking plan have been processed (i.e., it is terminated), the executor at block 584 transmits the taking plan (updated according to its execution) to the smartphone; at the same time, this information may also be transmitted to the PC of the doctor (to follow the therapy of the user) and, in an anonymous form, to the servers of the producers of the corresponding medicines (to perform statistical studies relating to their prescriptions individually and in association with other medicines). Passing to block 587 in the swim-lane of the smartphone, in response to the receiving the (updated) taking plan the unloading manager saves it by replacing its (not-updated) version in the taking plan file. An unloading cycle of the dispenser is then performed to unload any doses that have not been released (i.e., associated with the flag of missing release in the taking plan). The unloading cycle starts at block 590, wherein the unloading manager verifies whether a (current) unreleased dose, starting from the first one, remains to be processed. If so, the unloader at block 593 sends a (further) rotation command to the dispenser (according to the position of the entry of the unreleased dose in the taking plan) and displays an unloading notice on the screen of the smartphone (thereby entering a waiting condition). In response thereto, in the swim-lane of the dispenser the unloading agent at block 596 moves the wheel (via its controller) bringing the compartment containing the unreleased dose in front of the releasing opening and unlocks the pushbutton. Once the operator has unloaded the unreleased dose (by pressing the pushbutton to open the releasing opening thereby causing the fall of the corresponding dose onto the collecting surface, as detected by the controller of the pushbutton via its end-of-stroke sensor), the unloading agent at block 599 locks the pushbutton and sends a corresponding confirmation of unloading to the smartphone (for example, a message to the mobile application for managing the dispenser). In response thereto, the flow of activity returns to the block 587 in the swim-lane of the smartphone to repeat the same operations for a next unreleased dose. Referring again to the block 587, as soon as all unreleased doses have been processed (directly if there is no unreleased dose) the unloading cycle is terminated; the process then returns to the block 503 waiting for a next dispenser loading request.

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. In addition, the terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

For example, an embodiment provides a dispensing device for dispensing substances to be taken by a user. However, the dispensing device may be used to dispense substances of any type (for example, medicines, dietary products, food supplements) in any form (for example, pills, tablets, suppositories, sachets) for the taking by any user (for example, children, adults, elderly men, animals).

In an embodiment, the dispensing device comprises means for storing an indication of a taking plan of a plurality of doses of one or more substances (with the taking plan that comprises an indication of a taking time of each dose). However, the taking plan may be stored in any form (for example, file, database) and it may relate to any number of doses each comprising any number of items of any number of substances.

In an embodiment, the dispensing device comprises a plurality of compartments, each one for containing one of the doses. However, the compartments may be of any type (for example, with square, circular shape) and in any number.

In an embodiment, the dispensing device comprises means for providing a taking notice of each dose in response to the corresponding taking time. However, the taking notice may be of any type (for example, acoustic, visual, vocal or their combination).

In an embodiment, the dispensing device comprises means for releasing the dose corresponding to each taking notice from the corresponding compartment in response to a releasing command. However, the dose may be released in response to any releasing command (for example, with a touch key).

In an embodiment, the dispensing device comprises a plate having a collecting surface in a central zone thereof. However, the plate may be of any type (for example, square-shaped).

In one embodiment, the compartments are arranged in a peripheral zone of the plate. However, the compartments may be arranged in any way (for example, along a frame of any shape, completely or only partially).

In an embodiment, the means for releasing face towards the central zone of the plate for collecting the doses released thereby onto the collection surface. However, such an arrangement may be of any type (for example, with the means for releasing being flush or raised with respect to the plate).

In an embodiment, the collecting surface is concave. However, the concavity of the collecting surface may have any value; in any case, a basic implementation with a flat collecting surface is not excluded.

In an embodiment, each compartment has a constant width transversely to a radial direction of the plate. However, a different shape of the compartments (for example, widening towards the center of the plate) is not excluded.

In an embodiment, each compartment is sloping towards the collecting surface. However, the sloping may have any value (or it may also be completely missing, for example, if other means like a piston are available to facilitate the collection of the corresponding dose onto the collecting surface).

In an embodiment, the dispensing device comprises a wheel housing the compartments in the peripheral zone of the plate. However, the wheel may be made in any way (for example, with a transport chain of the compartments).

In an embodiment, the compartments are closed towards the collecting surface by a side surface of the plate. However, the compartments may be closed in any way (for example, individually for each compartment).

In an embodiment, the means for releasing comprise a releasing opening in the side surface of the plate for releasing the dose of each compartment placed in correspondence thereto and means for controlling the releasing opening by closing the releasing opening in a rest condition and opening the releasing opening in response to the releasing command. However, the means for releasing may be implemented differently (for example, with tilting compartments).

In an embodiment, the dispensing device comprises means for rotating the wheel thereby bringing the compartment of each dose in correspondence to the releasing opening in response to the corresponding taking time. However, the means for rotating may be implemented in any way (for example, with a gear rack); in any case, nothing prevents keeping the compartments fixed and moving the means for releasing.

In an embodiment, the means for controlling the releasing opening comprise a pushbutton arranged in the plate in correspondence to the releasing opening. However, the pushbutton may be of any shape and size, and it may be arranged anywhere else (for example, sideways).

In an embodiment, the pushbutton is maintained in front of the releasing opening by elastic means for closing the releasing opening and sinks into the collecting surface in opposition to the elastic means in response to a manual pressure for opening the releasing opening. However, the elastic means may be implemented in any way (for example, of rubber); the pushbutton may act in different ways (for example, remaining normally protruding from the collecting surface) or it may also be used only for operating a separate mechanism that opens/closes the releasing opening.

In an embodiment, the dispensing device comprises a cover integral with the plate for closing the compartments in front of the peripheral zone of the plate. However, the compartments may be closed in any way (for example, individually).

In an embodiment, the cover has a loading opening for loading the corresponding dose into each compartment placed in correspondence thereto. However, the loading opening may be arranged in a different position (for example, sideways).

In an embodiment, the dispensing device comprises means for unlocking the means for releasing (in response to the taking time) and for locking the means for releasing (in response to the release of the dose corresponding to the taking notice or to a missing release of the dose corresponding to the taking notice within a maximum delay from the taking notice). However, the means for locking/unlocking may be implemented in any way (for example, by disabling the touch key); in any case, nothing prevents leaving the means for releasing always unlocked.

In an embodiment, the dispensing device comprises means for storing an indication of missing release of each dose in response to a missing release of the dose within the maximum delay from the corresponding taking notice. However, nothing prevents storing different, additional or alternative information (for example, only the taking times of the doses) down to none.

In an embodiment, the dispensing device comprises means for transmitting a further taking notice of each dose to a mobile processing device of the user in response to the corresponding taking time (to cause the mobile processing device of the user to provide the further taking notice). However, the further taking notice may be of any type (either the same as or different from the taking notice) and it may be transmitted in any way (for example, through a mobile phone network or via a direct connection such as Bluetooth) to any mobile processing device (for example, a tablet); in any case, this function may be absent in a basic implementation.

In an embodiment, the dispensing device comprises means for receiving a confirmation of alternative taking of each dose from the mobile processing device of the user (in response to a command indicative of the taking of an alternative dose equal to the dose corresponding to further taking notice). However, the confirmation of alternative taking may be received in any way (see above); in any case, this function may be implemented in another way (for example, via web application) or be completely absent.

In an embodiment, the dispensing device comprises means for storing an indication of alternative taking of each dose in response to the corresponding confirmation of alternative taking. However, nothing prevents storing different, additional or alternative information (for example, the place of the alternative taking), down to none.

An embodiment provides an assistance system for facilitating the taking of substances by a user, which comprises the above-mentioned dispensing device and a processing device of a person in charge of the dispensing device. However, the processing device may be of any type (for example, a smartphone, a tablet, a laptop) of any operator (for example, a pharmacist, a nurse, the user himself).

In an embodiment, the dispensing device and the processing device of the person in charge are adapted to communicate to each other. However, this result may be obtained in any way (for example, through a mobile phone network, direct connection such as Bluetooth or even via wire).

In an embodiment, the processing device comprises means for storing an indication of a dosage of the substances to be taken by the user. However, the dosage may be stored in any form (for example, file, database) and it may be defined in any way (for example, by key-value pairs).

In an embodiment, the processing device comprises means for calculating the taking plan according to the dosage. However, the taking plan may be calculated in any way (for example, by assuming standard values for specific times such as the ones of meals); in any case, nothing prevents directly providing the taking plan in a simplified implementation.

In an embodiment, the processing device comprises means for controlling a loading of the doses into the dispensing device. However, a basic implementation wherein the loading is managed directly by the dispensing device is not excluded.

In an embodiment, for each dose the means for controlling the loading are adapted to send a loading command to the dispensing device to cause the dispensing device to bring a free one of the compartments to a loading condition and to provide a loading notice of the dose into the free compartment. However, the loading condition may be reached in any way (for example, by moving the loading opening towards the free compartment) and the loading notice may be of any type (for example, only on the processing device, only on the dispensing device or on both of them).

In an embodiment, the dispensing device comprises means for transmitting an indication of each unreleased dose associated with the indication of missing release to the processing device of the person in charge. However, this information may be transmitted in any way (for example, within the updated taking plan or stand-alone); in any case, nothing prevents sending different, additional or alternative information to any entity (for example, a server of a hospital to track the consumption of the medicines), down to none.

In an embodiment, the processing device of the person in charge comprises means for controlling an unloading of the dispensing device. However, such a function may also be implemented directly by the dispensing device (or be left entirely in charge of the operator in a basic implementation).

In an embodiment, for each unreleased dose the means for controlling the unloading are adapted to send an unloading command to the dispensing device to cause the dispensing device to bring the compartment of the unreleased dose to an unloading condition and to provide an unloading notice of the unreleased dose. However, the unloading condition may be reached in any way (for example, by moving the releasing opening towards the free compartment) and the unloading notice may be of any type (for example, only on the processing device, only on the dispensing device or on both of them).

An embodiment provides a processing device for use in such assistance system. However, the processing device may be of any type (see above); in any case, nothing prevents using the same solution for loading and/or unloading a dispensing device of a different type (even standard without the collection surface).

Generally, similar considerations apply if the dispensing device, the assistance system and the processing device each has a different structure or comprises equivalent components (for example, of different materials), or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

An embodiment provides a corresponding method (with steps for performing the operations of each of the elements described above).

Generally, similar considerations apply if the same solution is implemented with an equivalent method (by using similar steps with the same functions of more steps or portions thereof, removing some steps being non-essential, or adding further optional steps); moreover, the steps may be performed in a different order, concurrently or in an interleaved way (at least in part).

An embodiment provides a computer program configured for causing a computing machine to perform the above-mentioned method. An embodiment provides a computer program product comprising a computer readable storage medium embodying a computer program, the computer program being loadable into a working memory of a computing machine thereby configuring the computing machine to perform the same method. However, the computer program may be implemented only on the dispensing device, only on the processing device or on both of them. In any case, similar considerations apply if the computer program is structured in a different way; moreover, the program may be provided in any form (for example, external or resident software, firmware, or microcode either in object code or in source code, for example, to be compiled or interpreted) and on any computer readable (tangible) storage medium that may retain and store instructions for use by the computing machine. In any case, the solution according to an embodiment of the present disclosure lends itself to be implemented even with a hardware structure (for example, formed by electronic circuits integrated in one or more chips of semiconductor material), or with a combination of software and hardware suitably programmed or otherwise configured.

What is claimed is:

1. A dispensing device for dispensing substances to be taken by a user, wherein the dispensing device comprises:
    a memory for storing an indication of a taking plan of a plurality of doses of one or more substances, the taking plan comprising an indication of a taking time of each dose;
    a plurality of compartments each one for containing one of the doses,
    a signaling unit for providing a taking notice of each dose in response to the corresponding taking time;
    a plate having a collecting surface arranged at a central zone of the dispensing device, the dispensing device having a vertical axis located at a center of the dispensing device, wherein the vertical axis passes through the dispensing device's central zone;
    a wheel housing the compartments in a peripheral zone of the plate, the compartments being closed towards the collecting surface by a side surface of the plate;
    a releasing opening in the side surface of the plate facing towards the central zone for releasing the dose of each compartment placed in correspondence thereto towards the central zone, such that when a dose is released from the compartment through the releasing opening, the dose moves toward the dispensing device's vertical axis;
    a motor for rotating the wheel thereby bringing the compartment of each dose in correspondence to the releasing opening in response to the corresponding taking time;
    a pushbutton for controlling the releasing opening by closing the releasing opening in a rest condition and opening the releasing opening for releasing the dose corresponding to each taking notice from the corresponding compartment in response to a releasing command; and
    wherein the pushbutton is arranged in the plate in correspondence to the releasing opening, the pushbutton being maintained in front of the releasing opening by elastic means for closing the releasing opening and sinking into the collecting surface in opposition to the elastic means in response to a manual pressure for opening the releasing opening.

2. The dispensing device according to claim 1, wherein the collecting surface is concave.

3. The dispensing device according to claim 1, wherein each compartment has a constant width transversely to a radial direction of the plate.

4. The dispensing device according to claim 1, comprising a cover integral with the plate for closing the compartments in front of the peripheral zone of the plate, the cover having a loading opening for loading the corresponding dose into each compartment placed in correspondence thereto.

5. The dispensing device according to claim 1, comprising a latch for unlocking the pushbutton in response to the taking time and for locking the pushbutton in response to the release of the dose corresponding to the taking notice or to a missing release of the dose corresponding to the taking notice within a maximum delay from the taking notice, and a memory for storing an indication of missing release of each dose in response to the missing release of the dose within the maximum delay from the corresponding taking notice.

6. The dispensing device according to claim 1, comprising a transmitter for transmitting a further taking notice of each dose to a mobile processing device of the user in response to the corresponding taking time to cause the mobile processing device of the user to provide the further taking notice, a receiver for receiving a confirmation of alternative taking of each dose from the mobile processing device of the user in response to a command indicative of the taking of an alternative dose equal to the dose corresponding to the further taking notice and a memory for storing an indication of alternative taking of each dose in response to the corresponding confirmation of alternative taking.

* * * * *